(12) United States Patent  
Gauvry et al.

(10) Patent No.: US 9,580,404 B2  
(45) Date of Patent: Feb. 28, 2017

(54) SUBSTITUTED AZINES AS PESTICIDES

(71) Applicant: Novartis Tiergesundheit AG, Basel (CH)

(72) Inventors: Noelle Gauvry, Basel (CH); Francois Pautrat, Basel (CH)

(73) Assignee: Novartis Tiergesundheit AG, Indianapolis, IN (US)

( * ) Notice: Subject to any disclaimer, the term of this patent is extended or adjusted under 35 U.S.C. 154(b) by 0 days.

(21) Appl. No.: 15/156,406

(22) Filed: May 17, 2016

(65) Prior Publication Data

US 2016/0257665 A1   Sep. 8, 2016

Related U.S. Application Data

(62) Division of application No. 14/418,100, filed as application No. PCT/EP2013/066465 on Aug. 6, 2013, now Pat. No. 9,357,782.

(30) Foreign Application Priority Data

Aug. 8, 2012   (CH) ...................................... 1297/12

(51) Int. Cl.

| | | |
|---|---|---|
| *C07D 401/14* | (2006.01) |
| *A01N 43/40* | (2006.01) |
| *C07D 401/04* | (2006.01) |
| *C07D 403/12* | (2006.01) |
| *C07D 413/14* | (2006.01) |
| *A01N 43/54* | (2006.01) |
| *C07D 213/74* | (2006.01) |
| *C07D 401/12* | (2006.01) |
| *C07D 403/04* | (2006.01) |
| *C07D 403/14* | (2006.01) |
| *C07D 239/47* | (2006.01) |
| *C07D 239/48* | (2006.01) |
| *C07D 487/10* | (2006.01) |
| *A01N 43/60* | (2006.01) |
| *A01N 43/62* | (2006.01) |
| *A01N 43/84* | (2006.01) |
| *A01N 43/90* | (2006.01) |

(52) U.S. Cl.

CPC ........... *C07D 401/04* (2013.01); *A01N 43/40* (2013.01); *A01N 43/54* (2013.01); *A01N 43/60* (2013.01); *A01N 43/62* (2013.01); *A01N 43/84* (2013.01); *A01N 43/90* (2013.01); *C07D 213/74* (2013.01); *C07D 239/47* (2013.01); *C07D 239/48* (2013.01); *C07D 401/12* (2013.01); *C07D 401/14* (2013.01); *C07D 403/04* (2013.01); *C07D 403/12* (2013.01); *C07D 403/14* (2013.01); *C07D 413/14* (2013.01); *C07D 487/10* (2013.01)

(58) Field of Classification Search

CPC ..... C07D 401/14; A61K 31/444; A01N 43/40  
USPC ................. 544/364; 514/253.01, 253.12  
See application file for complete search history.

(56) References Cited

FOREIGN PATENT DOCUMENTS

| WO | 99/59979 | 11/1999 |
| WO | 2006/007864 | 1/2006 |
| WO | 2010/043315 | 4/2010 |

OTHER PUBLICATIONS

Koary, J., et al., "Preparation of pyrimidine derivatives with potential cardiotonic activity," Acta Pharmaceutica Hungarica, Hungarian Pharmaceutical Association, Budapest, HU, vol. 59, pp. 241-247 (Jan. 1, 1989).
STN Registry (2 pages) (Sep. 2008).

*Primary Examiner* — Deepak Rao  
(74) *Attorney, Agent, or Firm* — Joseph M. Pletcher

(57) ABSTRACT

The invention relates to compounds of the general formula (I), wherein the variable have the meanings as indicated in the claims, or a physiologically acceptable salt thereof. The active ingredients have advantageous pesticidal properties. They are especially suitable for controlling endoparasites in warm-blooded animals.

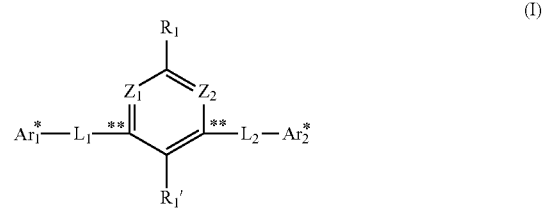

3 Claims, No Drawings

SUBSTITUTED AZINES AS PESTICIDES

FIELD OF THE INVENTION

This invention relates to novel pyridinyl or pyrimidinyl compounds, processes for their manufacture, their use in the control of endoparasites in and on animals, especially productive livestock and domestic animals, and furthermore pesticidal compositions which contain one or more of these compounds.

SUMMARY OF THE INVENTION

This present invention is directed to new compounds of formula

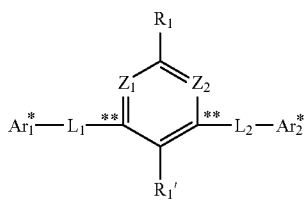

(I)

wherein one of $Z_1$ and $Z_2$ is N and the other one is N or $CR_1''$;

$R_1$, $R_1'$ and $R_1''$ are each independently of the other H, halogen, cyano, nitro, $C_1$-$C_4$-alkyl, $C_1$-$C_4$-haloalkyl, $C_1$-$C_4$-alkoxy, $C_1$-$C_3$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, halo-$C_1$-$C_4$-alkylsulfonyl, halo-$C_1$-$C_4$-alkylsulfinyl, halo-$C_1$-$C_4$-alkylsulfonylamino or benzylsulfonylamino;

$Ar_1$ and $Ar_2$ are each independently of the other
(i) phenyl which is substituted by 1 to 3 same or different substituents selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, benzylsulfonylamino, halo-$C_1$-$C_4$-alkylsulfonyl, halo-$C_1$-$C_4$-alkylsulfinyl and halodioxolyl; or
(ii) $C_5$-$C_6$-heteroaryl comprising 1 to 3 same or different heteroatoms selected from the group consisting of O, S and N, which is further unsubstituted or substituted by 1 to 3 same or different substituents selected from the group consisting of halogen, cyano, nitro, $C_1$-$C_4$-alkyl, $C_1$-$C_4$-haloalkyl, $C_1$-$C_4$-alkoxy, $C_1$-$C_3$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, $C_1$-$C_4$-alkylsulfonyl and $C_1$-$C_4$-alkylsulfinyl, $C_1$-$C_4$-alkylsulfonylamino, benzylsulfonylamino, halo-$C_1$-$C_4$-alkylsulfonyl and halo-$C_1$-$C_4$-alkylsulfinyl;

$L_1$ is a bifunctional linker radical of formula

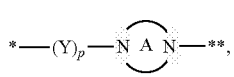

(IIa)

(IIb)

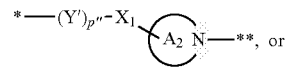

(IIc)

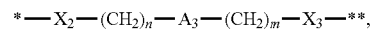

(IId)

$L_2$ is a bifunctional linker radical of formula

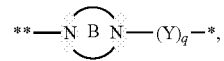

(IIIa)

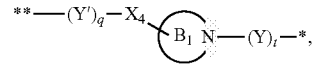

(IIIb)

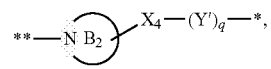

(IIIc)

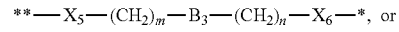

(IIId)

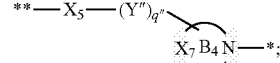

(IIIe)

A and B are each independently $C_3$-$C_8$-hetero-cycloalkylene or $C_5$-$C_{10}$-hetero-bicycloalkylene comprising two N-atoms, respectively which is each unsubstituted or substituted by $C_1$-$C_2$-alkyl;

$A_1$, $A_2$, $B_1$ and $B_2$ are each independently $C_3$-$C_8$-heterocycloalkylene comprising a N-atom, respectively;

$A_3$ and $B_3$ are each independently $C_2$-$C_6$-alkylene, $C_3$-$C_8$-cycloalkylene, $C_5$-$C_{10}$-bicycloalkylene or $C_5$-$C_{10}$-tricycloalkylene, wherein the cycloalkylene, bicycloalkylene or tricycloalkylene is each unsubstituted or substituted by $C_1$-$C_2$-alkyl;

$B_4$ is $C_3$-$C_8$-hetero-cycloalkylene comprising an N-atom and a further heteroatom $X_7$;

$X_1$, $X_3$, $X_4$ and $X_5$ are each independently of the other O or NR;

$X_2$, $X_6$ and $X_7$ are each independently O, S, S(O), S(O$_2$) or N(R);

Y, Y' and Y''' are each independently $CH_2$, C(O), S(O$_2$) or NR;

R is H or $C_1$-$C_4$-alkyl;

m and n are each independently of the other an integer 0, 1 or 2; and p, p', p'', q, q'' and t are each independently of the other an integer 0 or 1;

or a physiologically acceptable salt thereof.

This invention also provides a composition comprising a compound of formula (I), or a salt thereof, and at least one additional component selected from the group consisting of a surfactant, a solid diluent and a liquid diluent.

In one embodiment, this invention also provides a composition for controlling parasites, in particular endoparasites, comprising a biologically effective amount of a compound of formula (I), or a salt thereof, and at least one additional component selected from the group consisting of a surfactant, a solid diluent and a liquid diluent, said composition optionally further comprising a biologically effective amount of at least one additional biologically active compound or agent.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers.

"Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl isomers.

Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl isomers.

"N-alkylamino", "N,N-di-alkyamino", and the like, are defined analogously to the above examples.

"Cycloalkylene" Includes, for example, cyclopropylene, cyclobutylene, cyclopentylene, cyclohexylene, cycloheptylene or cyclooctylene, preferably cyclopropylene, cyclobutylene, cyclopentylene, cyclohexylene, and in particular cyclopentylene, cyclohexylene.

Examples of suitable bicyclalkylene and tricycloalkylene radicals according to the Invention are

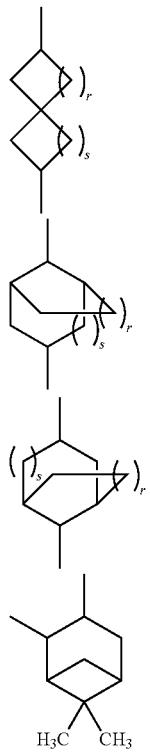

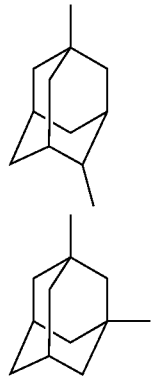

wherein r and s are each independently of the other an integer 0, 1 or 2.

Examples of preferred bicycloalkylene radicals are spiro-$C_7$-$C_{12}$-alkylenes, for example a spiro-[3.3]heptylene, spiro-[3.4]octylene or spiro-[4.4]nonylene radical.

Examples of bicycloaliphatic radicals comprising 1 or 2 heteroatoms are radicals of formula

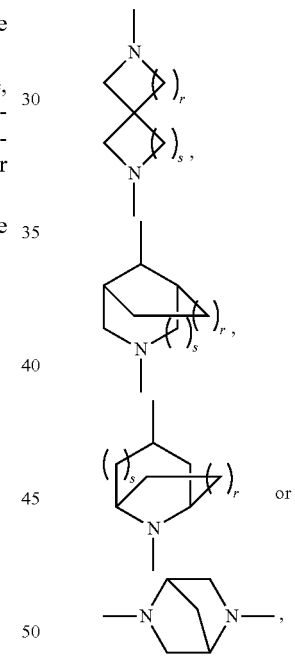

wherein r and s are each independently of the other an integer 0, 1 or 2. Examples of preferred heterobicycloalkylene radicals are spiro-diaza-$C_5$-$C_{10}$-alkylenes, such as 1,6- or 2,6-diaza spiro-[3.3]heptylene, 1,6- or 2,6-diaza spiro-[3.4]octylene or 1,7- or 2,7-diaza spiro-[4.4]nonylene.

The term heteroaryl denotes a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring", "aromatic heterocyclic ring". Unless otherwise indicated, heterocyclic rings and ring systems can be attached through any available carbon or nitrogen by replacement of a hydrogen on said carbon or nitrogen.

Examples of suitable heteroaryl radicals are pyridyl, pyrimidyl, s-triazinyl, 1,2,4-triazinyl, thienyl, furanyl, pyrryl, pyrazolyl, imidazolyl, thiazolyl, triazolyl, oxazolyl, thiadiazolyl or oxadiazolyl, preferably pyridyl, pyrimidyl, pyrryl, imidazolyl or thiazolyl, in particular 2-, 3- or 4-pyridyl.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$—, $ClCH_2$—, $CF_3CH_2$— and $CF_3CCl_2$—. The terms "halocycloalkyl", "haloalkoxy", "haloalkylthio", and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" Include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—.

The total number of carbon atoms in a substituent group is indicated by the "$C_i$-$C_j$" prefix where i and j are integers. For example, $C_1$-$C_4$ alkylsulfonyl designates methylsulfonyl through butylsulfonyl; $C_2$-alkoxyalkyl designates $CH_3OCH_2$; $C_3$-alkoxyalkyl designates, for example, $CH_3CH(OCH_3)$, $CH_3OCH_2CH_2$ or $CH_3CH_2OCH_2$; and $C_4$-alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$—.

When a compound is substituted with a substituent bearing a subscript that indicates the number of said substituents can exceed 1, said substituents (when they exceed 1) are independently selected from the group of defined substituents, e.g., $(R_2)_n$, is 1 or 2.

"Aromatic" indicates that each of the ring atoms is essentially in the same plane and has ap-orbital perpendicular to the ring plane, and in which $(4n+2)\pi$ electrons, where n is a positive integer, are associated with the ring to comply with Hückel's rule.

In the compounds of formula (I), $Z_1$ is preferably N. $Z_2$ is preferably N or CH, in particular N. According to one preferred embodiment $Z_1$ and $Z_2$ are each N. According to a further preferred embodiment $Z_1$ is N and $Z_2$ is CH.

$R_1$, $R_1'$ and $R_1''$ are each independently preferably H, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, amino or N-mono- or N,N-di-$C_1$-$C_4$-alkylamino, more preferably H, halogen, $C_1$-$C_2$-alkyl, $C_1$-$C_2$-alkoxy, $C_1$-$C_2$-alkylthio or N,N-di-$C_1$-$C_2$-alkylamino, and in particular H or methyl. $R_1$, $R_1'$ and $R_1''$ are each independently of the other more preferably H, halogen, $C_1$-$C_2$-alkyl, $C_1$-$C_2$-alkoxy, $C_1$-$C_2$-alkylthio or N,N-di-$C_1$-$C_2$-alkylamino. Most preferably two of $R_1$, $R_1'$ and $R_1''$ are H and the other one has one of the meanings as mentioned above including the preferences. In particular, $R_1$ and $R_1''$ are each H and $R_1'$ is H or methyl, in particular H.

$Ar_1$ as phenyl is preferably phenyl which is substituted by 1 or 2 same or different substituents selected from the group consisting of halogen, cyano, nitro, $C_1$-$C_2$-alkyl, $C_1$-$C_2$-haloalkyl, $C_1$-$C_2$-alkoxy or $C_1$-$C_2$-haloalkoxyl. A especially preferred phenyl radical $Ar_1$ is phenyl which is substituted by 1 or 2 same or different radicals selected from the group consisting of halogen and $C_1$-$C_2$-haloalkyl, in particular chlorine, fluorine or $CF_3$. A particularly preferred phenyl radical $Ar_1$ is phenyl mono-substituted by $CF_3$, especially 4-$CF_3$-phenyl.

A preferred heteroaryl radical $Ar_1$ or $Ar_2$ is 2-, 3- or 4-pyridyl or 2- or 3-thiophenyl which is each unsubstituted or substituted, for example, by methyl, ethyl, halogen, $CF_3$ or carboxy.

$Ar_2$ as phenyl is preferably phenyl which is substituted by 1 or 2 same or different substituents selected from the group consisting of halogen, cyano, nitro, $C_1$-$C_4$-alkyl, $C_1$-$C_2$-haloalkyl, $C_1$-$C_2$-alkoxy, $C_1$-$C_2$-haloalkoxyl, $C_1$-$C_2$-alkylthio, $C_1$-$C_2$-haloalkylthio, $C_1$-$C_2$-alkylsulfonyl, halo-$C_1$-$C_2$-alkylsulfonyl, amino, N-mono- and N,N-di-$C_1$-$C_4$-alkylamino, aminosulfonyl and $C_1$-$C_2$-alkylaminosulfonyl. An even more preferred phenyl radical $Ar_2$ is phenyl which is substituted by 1 or 2 same or different radicals selected from the group consisting of halogen, cyano, nitro, $C_1$-$C_4$-alkyl, $C_1$-$C_2$-haloalkyl, $C_1$-$C_2$-alkoxy, $C_1$-$C_2$-haloalkoxyl, $C_1$-$C_2$-haloalkylthio, $C_1$-$C_2$-alkylsulfonyl, halo-$C_1$-$C_2$-alkylsulfonyl, amino and $C_1$-$C_2$-alkylaminosulfonyl. A particularly preferred phenyl radical $Ar_2$ is phenyl which is substituted by 1 or 2 same or different radicals selected from the group consisting of halogen, cyano, nitro, $C_1$-$C_2$-haloalkyl, $C_1$-$C_2$-haloalkoxyl or $C_1$-$C_2$-haloalkylthio. An especially preferred phenyl radical $Ar_2$ is phenyl which is substituted by 1 or 2 same or different radicals selected from the group consisting of fluorine, cyano, nitro and $CF_3$. Examples of specifically preferred radicals $Ar_2$ are 4-nitro-3-$CF_3$-phenyl, 4-cyano-3-$CF_3$-phenyl, 3,4-di-$CF_3$-phenyl, 4-$CF_3$-3-fluorophenyl, 3-$CF_3$-4-fluorophenyl, 4-nitrophenyl, 3- and 4-$CF_3$-phenyl, 4-cyanophenyl, 4-$OCF_3$-phenyl and 4-$SCF_3$-phenyl, in particular 4-nitro-3-$CF_3$-phenyl.

The radicals $L_1$ and $L_2$ may be identical or different, in particular different.

Concerning the radical $L_1$ the following preferences apply:

(i) $X_1$ is preferably NH, $N(C_1$-$C_2$-alkyl) or O, in particular NH or $N(CH_3)$, especially NH.

(ii) p, p' and p" are each independently preferably 0.

(iv) m and n are each preferably 0.

(v) The variable A is preferably an unsubstituted heterocycloalkylene or hetero-bicycloalkylene radical, and especially $C_3$-$C_6$-hetero-cycloalkylene or $C_5$-$C_8$-hetero-bicycloalkylene comprising two N-atoms, respectively.

A is more preferably a radical

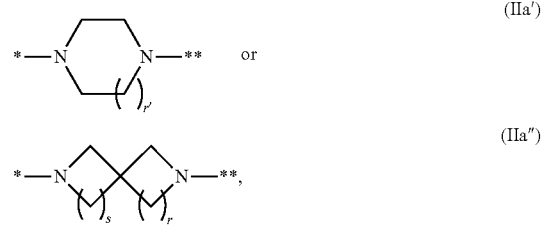

wherein s and r are each independently an integer 1 or 2, and r' is an integer 0, 1 or 2; in the above formulae, one of s and r is preferably 1 and the other one is 1 or 2, and r' is preferably 1 or 2, in particular 1. A particularly preferred radical A is a radical

(piperazine 1,4-diyl).

(vi) A preferred radical $A_1$ is of formula

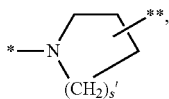

wherein s' is an integer 0, 1 or 2, in particular 1 or 2. Examples are a radical

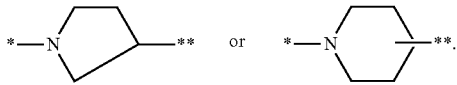

(vii) A preferred radical $A_2$ is of formula

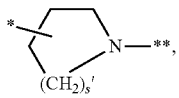

wherein s' is an integer 0, 1 or 2. Examples are a radical

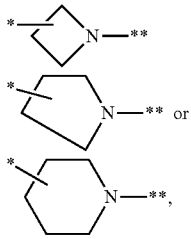

in particular a radical

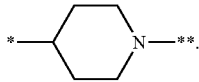

(viii)) A preferred radical $A_3$ is a $C_2$-$C_4$-alkylene or $C_3$-$C_6$-cycloalkylene radical, in particular 1,2-ethylene, 1,2- or 1,3-propylene, 1,3- or 1,4-butylene or $C_5$-$C_6$-cycloalkylene.

Preferably, $L_1$ is a radical of the formula

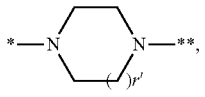 (IIa')

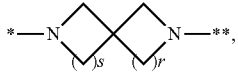 (IIa'')

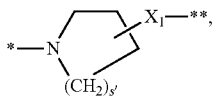 (IIb')

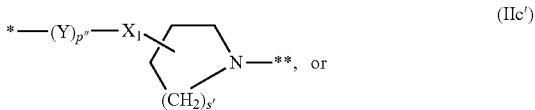 (IIc')

 (IId')

wherein $X_1$, $X_2$ and $X_3$ are each independently NH, N($C_1$-$C_2$-alkyl) or O, in particular each NH or N(CH$_3$), Y is —CH$_2$—, —NH—, —C(O)— or —S(O$_2$)—, in particular-, —C(O)— or —S(O$_2$)—, p" is 0 or 1, r' is 0, 1 or 2, r and s are each independently 1 or 2, s' is an integer 0, 1 or 2; and $A_3$ is $C_2$-$C_4$-alkylene or $C_3$-$C_6$-cycloalkylene.

Even more preferably, $L_1$ is a radical of formula (IIa'), (IIa''), (IIb'), (IIc') or (IId') above, wherein one of s and r is 1 and the other one is 1 or 2, r' is 0 or 1, s' is 1 or 2, $X_1$, $X_2$ and $X_3$ are each NH, p" is 0, and $A_4$ is $C_2$-$C_4$-alkylene or $C_5$-$C_6$-cycloalkylene.

Examples of specific radicals $L_1$ are

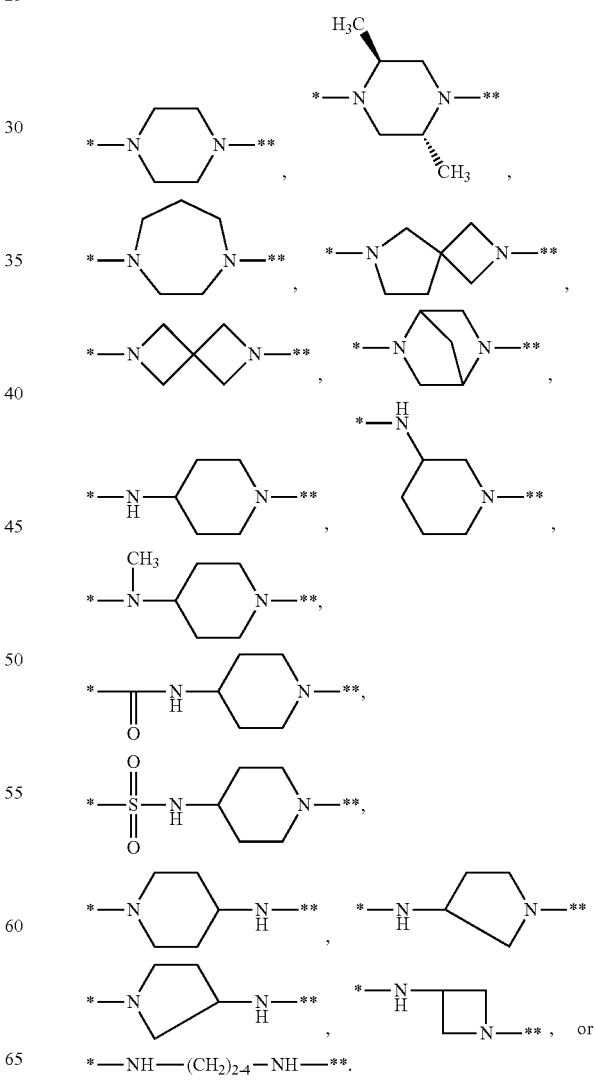

$*$—NH—(CH$_2$)$_{2-4}$—NH—$**$.

A particularly preferred radical $L_1$ is

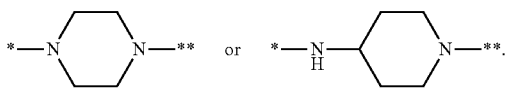

Concerning the radical $L_2$ the following preferences apply:
(i) $X_4$, $X_5$ and $X_7$ are each independently preferably NH, $N(C_1$-$C_2$-alkyl) or O, preferably NH or O, and in particular each O.
(ii) $X_6$ is preferably NH, $N(C_1$-$C_2$-alkyl) or O, in particular NH or O, especially NH.
(iii) q is preferably 0, q" is preferably 1, t is 0 or 1, in particular 0.
(iv) m and n are each preferably 0.
(v) Y is preferably methylene, —C(O)—, —NH— or —S(O$_2$)—, in particular methylene or —C(O)—; Y' is preferably C(O); Y" is preferably methylene.
(vi) B is preferably an unsubstituted hetero-cycloalkylene or hetero-bicycloalkylene radical, and especially $C_3$-$C_6$-hetero-cycloalkylene, in particular $C_3$-$C_4$-hetero-cycloalkylene, comprising two N-atoms. A particularly preferred radical B is a radical of formula

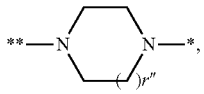

wherein r" is 0 or 1.
(vii) A preferred radical $B_1$ is of formula

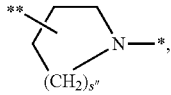

wherein s" is an integer 0, 1 or 2. Examples are a radical

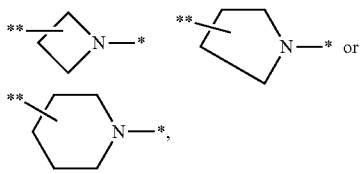

in particular a radical

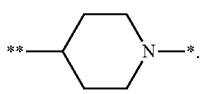

(viii) A preferred radical $B_2$ is of formula

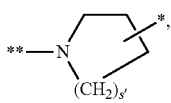

wherein s' is an integer 0, 1 or 2, in particular 1 or 2. Examples are a radical

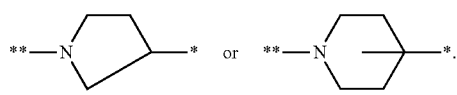

(ix) A preferred radical $B_3$ is a $C_2$-$C_4$-alkylene or $C_3$-$C_6$-cycloalkylene radical, in particular $C_3$-$C_6$-cycloalkylene. A particularly preferred radical $B_4$ is

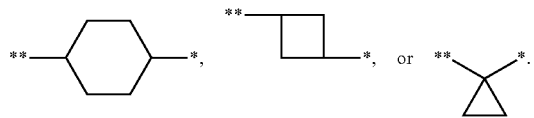

(x) A preferred radical $B_4$ is a hetero-$C_3$-$C_4$-cycloalkylene radical, more preferably hetero-$C_3$-$C_4$-cycloalkylene radical comprising heteroatoms $X_5$ and $X_6$, wherein $X_5$ and $X_6$ are each independently O or NH. A particularly preferred radical $B_4$ is

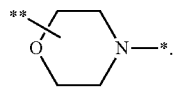

$L_2$ is preferably a radical of formula

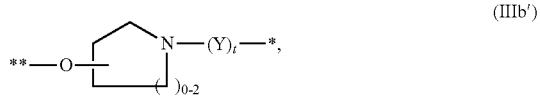 (IIIb')

 (IIIc')

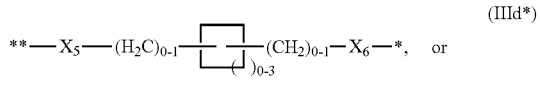 (IIId*)

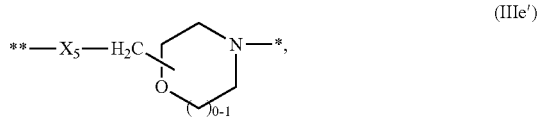 (IIIe')

wherein Y is —CH$_2$—, —NH—, —C(O)— or —S(O)$_2$—, t is 0 or 1, and $X_5$ and $X_6$ are each independently O or NH or $N(C_1$-$C_2$-alkyl).

$L_2$ is even more preferably a radical of formula

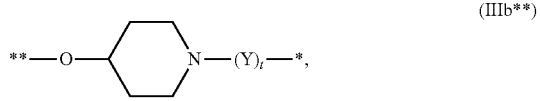 (IIIb**)

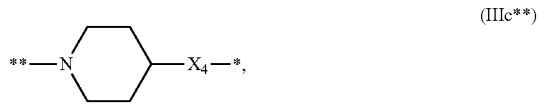 (IIIc**)

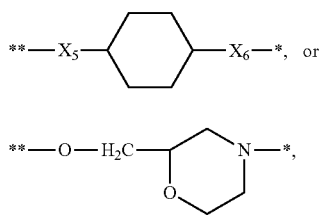

wherein Y is —CH₂—, —NH—, —C(O)— or —S(O)₂—, t is 0 or 1, and X₄, X₅ and X₆ are each independently O or NH or N(CH₃).

L₂ is particularly preferred a radical of the formula (IIIb) or (IIId) above; especially preferred are those radicals of the formula (IIIb) or (IIId), wherein Y is —CH₂— or —C(O)—, t is 0 or 1, in particular 0, X₅ is O, and X₆ is NH or O, in particular NH.

Examples of specific radicals L₂ are

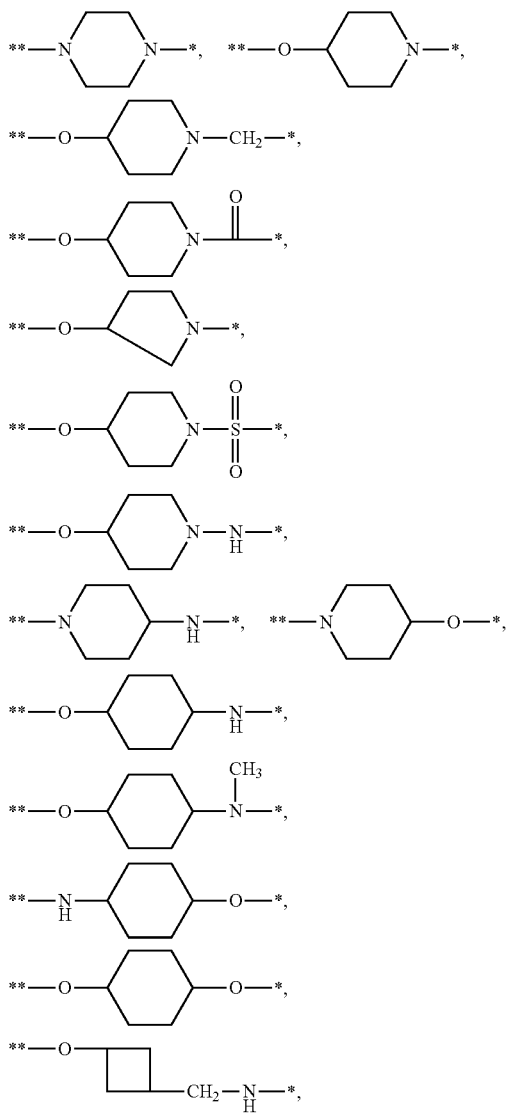

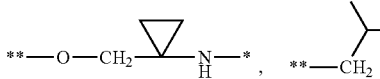

Examples of specifically preferred radicals L₂ are

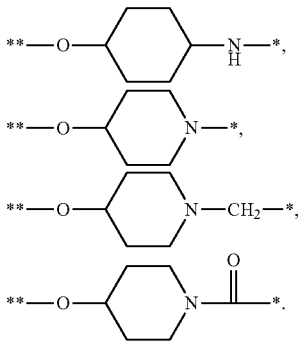

In the above radicals L₂, in case of a cyclohexylene radical the trans-configuration is in general preferred.

A preferred embodiment of the present invention relates to compounds of formula

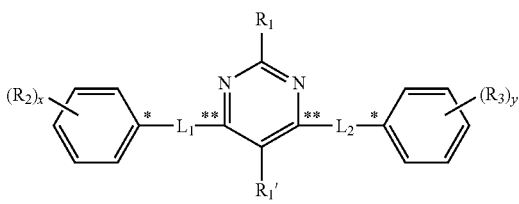

wherein one of R₁ and R₁' is H and the other one is H, halogen, C₁-C₄-alkyl, C₁-C₄-alkoxy, C₁-C₄-alkylthio, or amino, N-mono- or N,N-di-C₁-C₄-alkylamino;

x and y are each independently of the other 1, 2 or 3;

R₂ and R₃ are each independently of the other halogen, cyano, nitro, C₁-C₄-alkyl, C₁-C₄-haloalkyl, C₁-C₄-alkoxy, C₁-C₄-haloalkoxyl, C₁-C₄-alkylthio, halo-C₁-C₄-alkylthio, SF₅, amino, N-mono- or N,N-di-C₁-C₄-alkylamino, aminosulfonyl, N-mono- or N,N-di-C₁-C₄-alkylaminosulfonyl, C₁-C₄-alkylsulfonyl, C₁-C₄-alkylsulfinyl, C₁-C₄-alkylsulfonylamino, benzylsulfonylamino, halo-C₁-C₄-alkylsulfonyl, halo-C₁-C₄-alkylsulfinyl and halodioxolyl; wherein, if x or y is 2 or 3, the two or three radicals R₂ or R₃ each may be same or different;

L₁ is a radical of formula

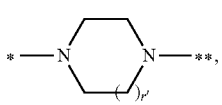

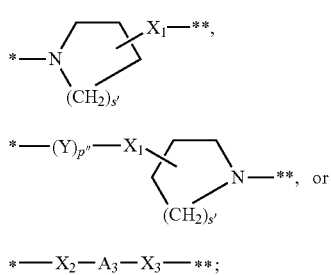 (IIb')

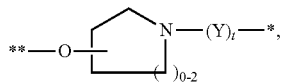 (IIc')

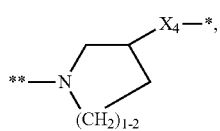 (IId')

$L_2$ is a radical of formula

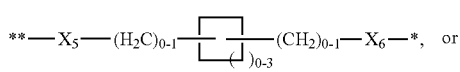 (IIIb')

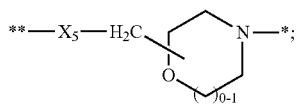 (IIIc')

(IIId')

(IIIe')

Y is —CH$_2$—, —NH—, —C(O)— or —S(O)$_2$—;

$X_1$, $X_2$, $X_3$, $X_4$, $X_5$ and $X_6$ are each independently O, NH or N(C$_1$-C$_2$-alkyl);

r' is 0, 1 or 2, r and s are each independently 1 or 2, s' is each independently an integer 0, 1 or 2; p" is 0 or 1; t is 0 or 1;

and $A_3$ is C$_2$-C$_4$-alkylene or C$_3$-C$_6$-cycloalkylene;

or a physiologically acceptable salt thereof.

A particularly preferred embodiment of the present invention relates to compounds of formula (Ia) above, wherein $R_1$ is H and $R_1'$ is H, halogen, C$_1$-C$_4$-alkyl, C$_1$-C$_4$-alkoxy, C$_1$-C$_4$-alkylthio, or amino, N-mono- or N,N-di-C$_1$-C$_4$-alkylamino, in particular H or methyl;

x and y are each Independently of the other 1 or 2;

$R_2$ and $R_3$ are each independently of the other halogen, cyano, nitro, C$_1$-C$_4$-alkyl, C$_1$-C$_2$-haloalkyl, C$_1$-C$_2$-alkoxy, C$_1$-C$_2$-haloalkoxyl, C$_1$-C$_2$-alkylthio, C$_1$-C$_2$-haloalkylthio, C$_1$-C$_2$-alkylsulfonyl, halo-C$_1$-C$_2$-alkylsulfonyl, amino, N-mono- and N,N-di-C$_1$-C$_4$-alkylamino, aminosulfonyl and C$_1$-C$_2$-alkylaminosulfonyl; wherein, if x or y is 2, the two radicals $R_2$ or $R_3$ each may be same or different;

$L_1$ is a radical

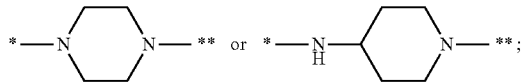

and $L_2$ is a radical

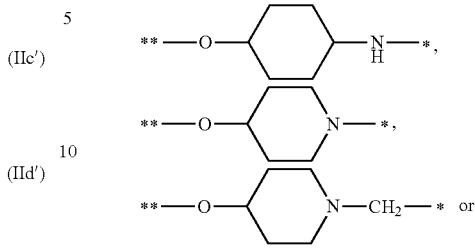

or a physiologically acceptable salt thereof.

A especially preferred embodiment of the present invention relates to compounds of formula (Ia) above, wherein $R_1$ is H and $R_1'$ is H or methyl;

x is one or two, in particular 1, and y is 1 or 2, in particular 2;

$R_2$ is halogen or C$_1$-C$_2$-haloalkyl, in particular CF$_3$;

$R_3$ is of fluorine, cyano, nitro or CF$_3$, in particular nitro or CF$_3$;

wherein, if x or y is 2, the two radicals $R_2$ or $R_3$ are each different;

$L_1$ is a radical $L_1$ is

$L_2$ is a radical

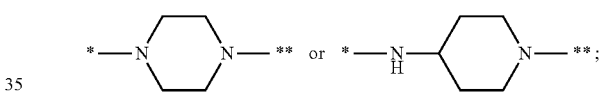

or a physiologically acceptable salt thereof.

Further preferred embodiments of the present invention relate to compounds of formula

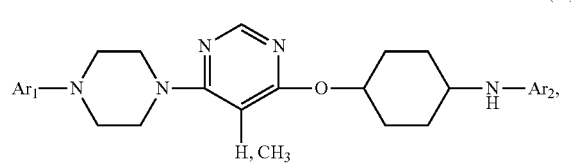 (Ib)

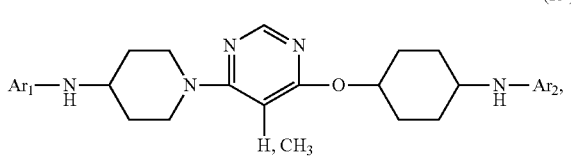 (Ib')

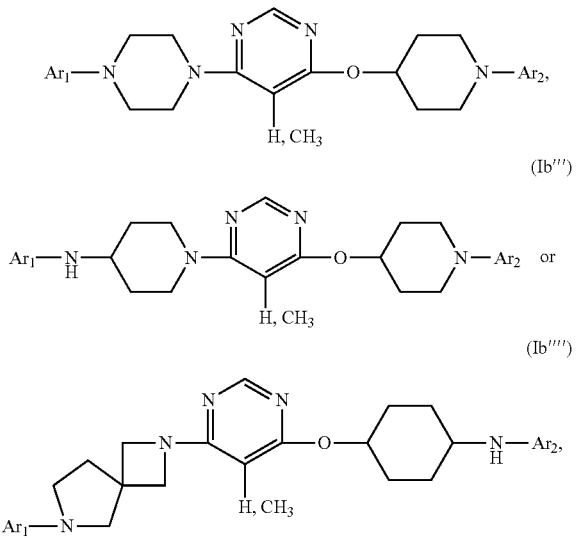

wherein for Ar$_1$ and Ar$_2$ each the above-given meanings and preferences apply.

Especially preferred compounds are of formula (Ib), (Ib'), (Ib''), (Ib''') or (Ib'''') wherein Ar$_1$ is 4-CF$_3$-phenyl, and Ar$_2$ is 4-nitro-3-CF$_3$-phenyl, 4-cyano-3-CF$_3$-phenyl, 3,4-di-CF$_3$-phenyl, 4-CF$_3$-3-fluorophenyl, 3-CF$_3$-4-fluorophenyl, 4-nitrophenyl, 3- or 4-CF$_3$-phenyl, 4-cyanophenyl, 4-OCF$_3$-phenyl or 4-SCF$_3$-phenyl, in particular 4-nitro-3-CF$_3$-phenyl.

The compounds of formula (I) may be prepared, for example, by reacting a compound of formula

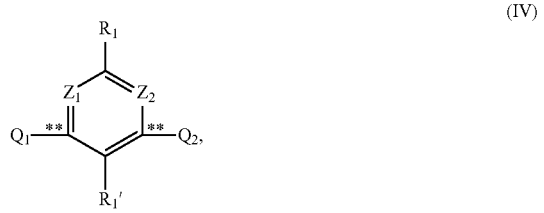

wherein R$_1$, R$_1$', Z$_1$ and Z$_2$ are each as defined above and Q$_1$ and Q$_2$ are each independently a leaving group, for example halogen, in particular chlorine, successively with a compound each of formulae Ar$_1$-L$_1$-H    (Va), and H-L$_2$-Ar$_2$    (Vb)

wherein Ar$_1$, Ar$_2$, L$_1$ and L$_2$ are each as defined above, in a manner known per se, in particular in a medium which is suitable for aromatic nucleophilic substitution of a pyridine or pyrimidine of the above formula (IV). The reaction conditions vary depending on the reactivity of the compound of formula (Va) or (Vb) employed. A compound of formula (Va) or (Vb) with a terminal hydroxyl or thiol group reacts more readily with a compound of formula (IV)—for example in an aprotic dipolar solvent at room temperature—than a compound of formula (Va) or (Vb) with a terminal primary or secondary amino group, which is preferably reacted in dipolar aprotic solvents at higher temperatures such as 70 to 120° C., optionally in the presence of a catalyst such as Pd(OAc)$_2$, RuPhos and the like. Specific examples of these aromatic nucleophilic substitution reactions of halopyridines and halopyrimidines are known, for example, from J. Med. Chem. 2011, Vol 54, p. 6563-6585, J. Med. Chem. 2009, Vol 52, p. 5999-6011, or Chem. Science 2011, Vol. 2, p. 57-68.

The compounds of formula (IV) are known or can be obtained by methods known per se. The compounds of formula (Va) and (Vb) likewise may be obtained by methods known per se, for example by aromatic nucleophilic substitution of a halogenated compound Ar$_1$ or Ar$_2$ with a compound H-L$_1$-H or H-L$_2$H.

Salts of compounds I may be produced in known manner. Acid addition salts of compounds I, for example, are obtainable by treatment with a suitable acid or a suitable ion exchange reagent, and salts with bases are obtainable by treatment with a suitable base or a suitable ion exchange reagent.

Salts of compounds I can be converted into the free compounds I by the usual means, acid addition salts e.g. by treating with a suitable basic composition or with a suitable ion exchange reagent, and salts with bases e.g. by treating with a suitable acid or a suitable ion exchange reagent.

Salts of compounds I can be converted into other salts of compounds I in a known manner; acid addition salts can be converted for example into other acid addition salts, e.g. by treating a salt of an Inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds I with salt-forming characteristics can be obtained in free form or In the form of salts.

Compounds I can also be obtained in the form of their hydrates and/or also can include other solvents, used for example where necessary for the crystallisation of compounds present in solid form.

The compounds of formula I may be optionally present as optical and/or geometric isomers or as a mixture thereof. The invention relates both to the pure isomers and to all possible isomeric mixtures, and is hereinbefore and hereinafter understood as doing so, even if stereochemical details are not specifically mentioned in every case.

In some embodiments a compound of formula (I) may have two or more conformational structures. For example, a compound of formula (I), wherein L$_2$ is a radical of formula

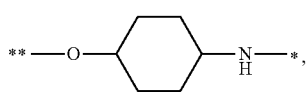

can have the cis configuration

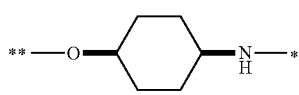

or, preferably, the trans configuration

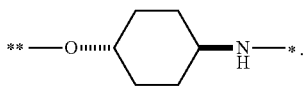

In general, a compound structure that does not indicate a particular conformation, is intended to encompass all of the possible conformational isomers of the compound, as well as compositions comprising fewer than all the possible conformational isomers or just one isomer. In case of a disubstituted cyclohexyl ring the trans isomer is generally preferred.

Diastereoisomeric mixtures of compounds of formula (I), which are obtainable by the process or in another way, may be separated in known manner, on the basis of the physical-chemical differences in their components, into the pure diastereoisomers, for example by fractional crystallisation, distillation and/or chromatography.

Splitting of mixtures of enantiomers, that are obtainable accordingly, into the pure isomers, may be achieved by known methods, for example by recrystallisation from an optically active solvent, by chromatography on chiral adsorbents, e.g. high-pressure liquid chromatography (HPLC) on acetyl cellulose, with the assistance of appropriate microorganisms, by cleavage with specific immobilised enzymes, through the formation of inclusion compounds, e.g. using chiral crown ethers, whereby only one enantiomer is complexed.

The compounds (I) according to the invention are notable for their broad activity spectrum and are valuable active ingredients for use in pest control, including in particular the control of endo- and ecto-parasites, especially helminths, in and on warm-blooded animals, especially livestock and domestic animals, whilst being well-tolerated by warm-blooded animals and fish.

In the context of the present invention, ectoparasites are understood to be in particular insects, mites and ticks. These include insects of the order: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga camaria, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Stomoxys calcitrans, Haematobla irritans* and midges (Nematocera), such as Culicidae, Simuliidae, Psychodidae, but also blood-sucking parasites, for example fleas, such as *Ctenocephalides felis* and *Ctenocephalides canis* (cat and dog fleas), *Xenopsylla cheopis, Pulex irritans, Dermatophilus penetrans,* lice, such as *Damalina ovis, Pediculus humanis,* biting flies and horse-flies (Tabanidae), *Haematopota* spp. such as *Haematopota pluvialis, Tabanidea* spp. such as *Tabanus nigrovittatus, Chrysopsinae* spp. such as *Chrysops caecutiens,* tsetse flies, such as species of *Glossinia,* biting insects, particularly cockroaches, such as *Blatella germanica, Blatta orientalis, Periplaneta americana,* mites, such as *Dermanyssus gallinae, Sarcoptes scablei, Psoroptes ovis* and *Psorergates* spp. and last but not least ticks. The latter belong to the order Acarina. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Omithodoros* and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

The compounds of formula (I) according to the Invention are also active against all or individual development stages of animal pests showing normal sensitivity, as well as those showing resistance, such as insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds (I) can also be used against hygiene pests, especially of the order Diptera of the families Sarcophagidae, Anophilidae and Culicidae; the orders Orthoptera, Dictyoptera (e.g. the family Blattidae) and Hymenoptera (e.g. the family Formicidae).

In particular, the compounds are effective against helminths, in which the endoparasitic nematodes and trematodes may be the cause of serious diseases of mammals and poultry, e.g. sheep, pigs, goats, cattle, horses, donkeys, dogs, cats, guinea-pigs or exotic birds, in particular sheep or especially cattle. Typical nematodes of this indication are: *Haemonchus, Trichostrongylus, Ostertagia, Nematodirus, Cooperia, Ascaris, Bunostonum, Oesophago-stonum, Charbertia, Trichuris, Strongylus, Trichonema, Dictyocaulus, Capillaria, Heterakis, Toxocara, Ascaridia, Oxyuris, Ancylostoma, Uncinaria, Toxascaris Dirofilaria, Acanthocheilonema* and *Parascaris.* The trematodes include, in particular, the family of Fasciolideae, especially *Fasciola hepatica.*

It could also be shown surprisingly and unexpectedly that the compounds of formula (I) have exceptionally high efficacy against nematodes that are resistant to many active substances. This can be demonstrated in vitro by the LDA test and in vivo for example in Mongolian gerbils. It was shown that amounts of active substance which kill sensitive strains of *Haemonchus contortus* or *Trichostrongylus colubriformis,* are also sufficiently effective at controlling corresponding strains that are resistant to benzimidazoles or levamisole.

Certain pests of the species *Nematodirus, Cooperia* and *Oesophagostonum* infest the intestinal tract of the host animal, while others of the species *Haemonchus* and *Ostertagia* are parasitic in the stomach and those of the species *Dictyocaulus* are parasitic in the lung tissue. Parasites of the families Filariidae and Setariidae may be found in the internal cell tissue and in the organs, e.g. the heart, the blood vessels, the lymph vessels and the subcutaneous tissue. A particularly notable parasite is the heartworm of the dog, *Dirofilaria immitis.* The compounds of formula (I) are highly effective against these parasites. The pests which may be controlled by the compounds of formula I also include those from the class of Cestoda (tapeworms), e.g. the families Mesocestoidae, especially of the genus *Mesocestoides,* in particular *M. lineatus; Dilepidide,* especially *Dipylidium caninum, Joyeuxiella* spp., in particular *Joyeuxiella pasquali,* and *Diplopylidium* spp., and Taeniidae, especially *Taenia pisiformis, Taenia cervi, Taenia ovis, Taneia hydatigena, Taenia multiceps, Taenia taeniaeformis, Taenia seria-*

*lis*, and *Echinocuccus* spp., most preferably *Taneia hydatigena, Taenia ovis, Taenia multiceps, Taenia serialis; Echinocuccus granulosus* and *Echinococcus granulosus* and *Echinococcus multilocularis*, as well as *Multiceps multiceps*.

Most particularly, *Taenia hydatigena, T. pisiformis, T. ovis, T. taeniaeformis, Multiceps multiceps, Joyeuxiella pasquali, Dipylidium caninum, Mesocestoides* spp., *Echinococcus granulosus* and *E. multilocularis* are controlled on or in dogs and cats simultaneously with *Dirofilaria* ssp., *Ancylostoma* ssp., *Toxocara* ssp. and/or *Trichuris vulpis*. Equally preferred, *Ctenocephalides felis* and/or *C. canis* are simultaneously controlled with the above-mentioned nematodes and cestodes.

Furthermore, the compounds of formula (I) are suitable for the control of human pathogenic parasites. Of these, typical representatives that appear in the digestive tract are those of the species *Ancylostoma, Necator, Ascaris, Strongyloides, Trichinella, Capillaria, Trichuris* and *Enterobius*. The compounds of the present invention are also effective against parasites of the species *Wuchereria, Brugia, Onchocerca* and *Loa* from the family of Filariidae, which appear in the blood, in the tissue and in various organs, and also against *Dracunculus* and parasites of the species *Strongyloides* and *Trichinella*, which infect the gastrointestinal tract in particular.

The good pesticidal activity of the compounds of formula (I) according to the invention corresponds to a mortality rate of at least 50-60% of the pests mentioned. In particular, the compounds of formula (I) are notable for the exceptionally long duration of efficacy.

The compounds of formula (I) are preferably employed in unmodified form or preferably together with the adjuvants conventionally used in the art of formulation and may therefore be processed in a known manner to give, for example, emulsifiable concentrates, directly dilutable solutions, dilute emulsions, soluble powders, granules or microencapsulations in polymeric substances. As with the compositions, the methods of application are selected in accordance with the intended objectives and the prevailing circumstances.

The formulation, i.e. the agents, preparations or compositions containing the active ingredient of formula (I), or combinations of these active ingredients with other active ingredients, and optionally a solid or liquid adjuvant, are produced in a manner known per se, for example by intimately mixing and/or grinding the active ingredients with spreading compositions, for example with solvents, solid carriers, and optionally surface-active compounds (surfactants).

The solvents in question may be: alcohols, such as ethanol, propanol or butanol, and glycols and their ethers and esters, such as propylene glycol, dipropylene glycol ether, ethylene glycol, ethylene glycol monomethyl or -ethyl ether, ketones, such as cyclohexanone, isophorone or diacetanol alcohol, strong polar solvents, such as N-methyl-2-pyrrolidone, dimethyl sulfoxide or dimethylformamide, or water, vegetable oils, such as rape, castor, coconut, or soybean oil, and also, if appropriate, silicone oils.

Preferred application forms for usage on warm-blooded animals in the control of helminths include solutions, emulsions, suspensions (drenches), food additives, powders, tablets including effervescent tablets, boli, capsules, microcapsules and pour-on formulations, whereby the physiological compatibility of the formulation excipients must be taken into consideration.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), glidants and disintegrants.

If the anthelminthics are present in the form of feed concentrates, then the carriers used are e.g. performance feeds, feed grain or protein concentrates. Such feed concentrates or compositions may contain, apart from the active ingredients, also additives, vitamins, antibiotics, chemotherapeutics or other pesticides, primarily bacteriostats, fungistats, coccidiostats, or even hormone preparations, substances having anabolic action or substances which promote growth, which affect the quality of meat of animals for slaughter or which are beneficial to the organism in another way. If the compositions or the active ingredients of formula I contained therein are added directly to feed or to the drinking troughs, then the formulated feed or drink contains the active ingredients preferably in a concentration of ca. 0.0005 to 0.02% by weight (5-200 ppm).

The compounds of formula (I) according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. If the range of activity is to be extended to endoparasites, e.g. wormers, the compounds of formula I are suitably combined with substances having endoparasitic properties. Of course, they can also be used in combination with antibacterial compositions. Since the compounds of formula I are adulticides, i.e. since they are effective in particular against the adult stages of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula (I).

Suitable partners in the mixture may be biocides, e.g. the insecticides and acaricides with a varying mechanism of activity, which are known to the person skilled in the art, e.g. chitin synthesis inhibitors, growth regulators; active ingredients which act as juvenile hormones; active ingredients which act as adulticides; broad-band insecticides, broad-band acaricides and nematicides; and also the well-known anthelminthics and insect- and/or acarid-deterring substances, repellents, detachers and synergists.

Non-limitative examples of suitable insecticides and acaricides are mentioned in WO 2009/071500, compounds Nos. 1-284 on pages 18-21.

Non-limitative examples of suitable anthelminthics are mentioned in WO 2009/071500, compounds (A1)-(A31) on page 21.

Non-limitative examples of suitable repellents and detachers are mentioned in WO 2009/071500, compounds (R1)-(R3) on page 21 and 22.

Non-limitative examples of suitable synergists are mentioned in WO 2009/071500, compounds (S1)-(S3) on page 22.

Accordingly, a further essential aspect of the present invention relates to combination preparations for the control of parasites on warm-blooded animals, characterised in that they contain, in addition to a compound of formula (I), at least one further active ingredient having the same or different sphere of activity and at least one physiologically acceptable carrier. The present invention is not restricted to two-fold combinations.

In one embodiment of the invention, the compound of formula (I) is used in combination with one or more further anthelmintic agents. Such a combination may reduce further the likelihood of resistance developing. Suitable further anthelmintic agents include.

The Examples further illustrate the invention.

Characterization data reported thereafter in the last column of Tables 1-3 is done using a Waters Autopurification (HPLC/MS) system with a reversed phase column (XTerra®, MS C18 5 μm, 50×4.6 mm). The samples are characterized by m/z and retention time. The retention times relate in each case to the use of a solvent system comprising two different solvents, solvent A: $H_2O+0.01\%$ HCOOH, and solvent B: $CH_3CN+0.01\%$ HCOOH). Said two solvents A and B are employed at a flow rate of 2.00 ml/min with a time-dependent gradient as given in the Table:

| Time [min] | A [%] | B [%] |
|---|---|---|
| 0 | 70.0 | 30.0 |
| 0.5 | 70.0 | 30.0 |
| 0.75 | 55.1 | 44.9 |
| 1 | 41.2 | 58.8 |
| 1.25 | 30.3 | 69.7 |
| 1.5 | 21.4 | 78.6 |
| 1.75 | 13.8 | 86.2 |
| 2 | 9.0 | 91.0 |
| 2.25 | 6.0 | 94.0 |
| 2.5 | 5.0 | 95.0 |
| 2.8 | 5.0 | 95.0 |
| 2.9 | 70.0 | 30.0 |
| 3.0 | 70.0 | 30.0 |

EXAMPLE 1

No. 23 in the Table Below

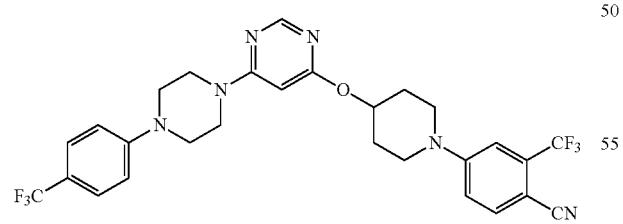

2.5 g of 4-hydroxypiperidine and 4.7 g of 4-fluoro-2-(trifluromethyl)-benzonitrile were reacted 5 h at 95° C. in DMSO to form 4-(4-hydroxypiperidin-1-yl)-2-(trifluoromethyl)-benzonitrile which, after aqueous work-up and Isolation was dissolved in 10 ml DMF was reacted at 5° C. with 250 mg of NaH (60% w/w) for 30 min. Then at 0° C., 2 g of 4,6-dichloropyrimidine were added to the mixture, stirred 30 min at room temperature to form 4-{4-[(6-chloropyrimidin-4-yl)oxy]piperidin-1-yl}-2-(trifluoromethyl)-benzonitrile. 115 mg of isolated by aqueous work-up and Isolation by column chromatography were reacted with 138 mg of 1-[4-(trifluoromethyl)-phenyl]piperazine in presence of 117 mg of $CsCO_3$, 7 mg of $Pd(OAc)_2$, 21 mg of RuPhos in 2 ml of tert-BuOH at 85° C. over night to provide compound No. 23 after isolation by aqueous workup and column chromatography.

EXAMPLE 2

No 88 in the table below

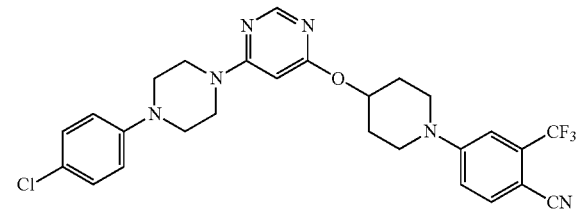 [SMILES: N#Cc1ccc(N2CCC(Oc3cc(N4CCN(c5ccc(Cl)cc5)CC4)ncn3)CC2)cc1C(F)(F)F]

100 mg of 4-{4-[(6-chloropyrimidin-4-yl)oxy]piperidin-1-yl}-2-(trifluoromethyl)-benzonitrile prepared using the procedure described in Example 1 was reacted with 84 mg of 1-(4-Chlorophenyl)piperazine dihydrochloride in 2 ml of NMP in presence of 0.18 ml of triethylamine for 6 h at 80° C. to provide compound No. 88 after isolation by column chromatography.

The substances as shown in the following Tables 1 to 3 are prepared analogously to the above-described methods. Therein, the following abbreviations are used for the radicals *-$L_1$- and -$L_2$-*:

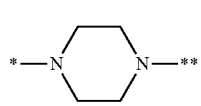
L1-A

L1-B

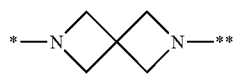
L1-C

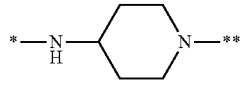
L1-D

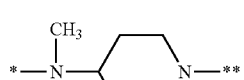
L1-E

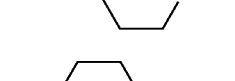
L1-F

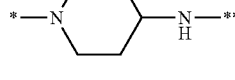
L1-G

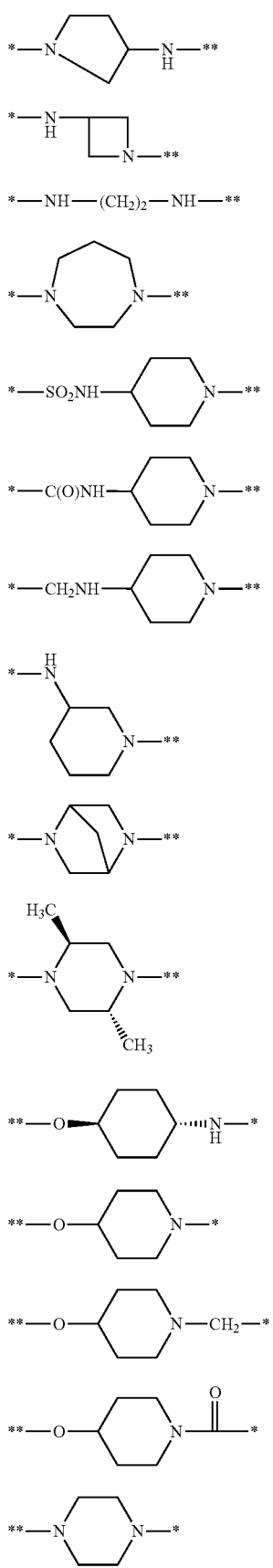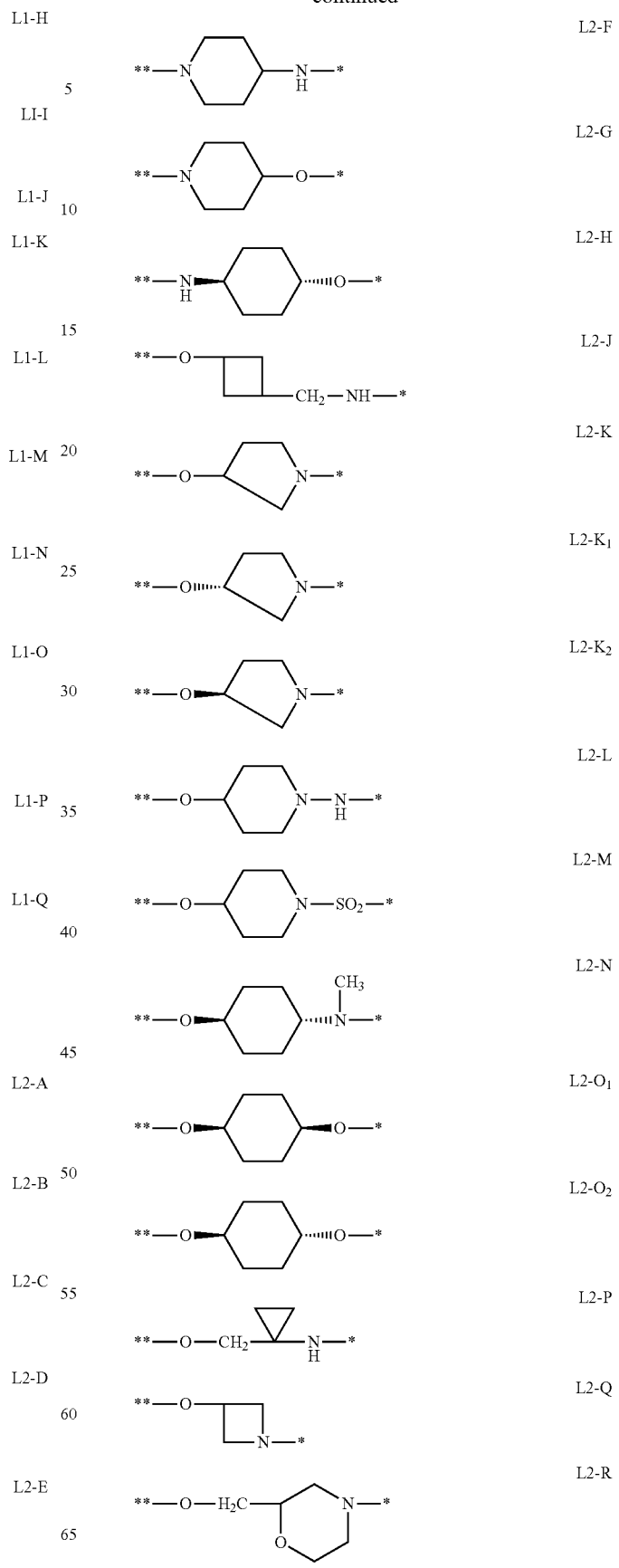

TABLE 1

Ar₁*—L₁—[pyrimidine]—L₂—Ar₂*

| No. | Ar₁ | L₁ | Ar₂ | L₂ | Retention Time (min.)/[MH]+ |
|---|---|---|---|---|---|
| 1 | 4-CF3-phenyl | L1-A | 4-CF3-phenyl | L2-E | |
| 2 | 3-CF3-phenyl | L1-A | 3-CF3-4-nitrophenyl | L2-A | 2.26/611.3 |
| 3 | 4-CF3-phenyl | L1-A | 3-CF3-4-nitrophenyl | L2-F | 1.4/595.9 |
| 4 | 3-CF3-phenyl | L1-A | 3-CF3-4-nitrophenyl | L2-A | 2/610.9 |
| 5 | 4-CF3-phenyl | L1-A | 3-CF3-4-nitrophenyl | L2-B | 2/596.9 |
| 6 | 4-CF3-phenyl | L1-D | 3-CF3-4-nitrophenyl | L2-A | 2.1/624.9 |
| 7 | 4-CF3-phenyl | L1-F | 3-CF3-4-nitrophenyl | L2-A | 2.1/625 |
| 8 | 4-CF3-phenyl | L1-K | 3-CF3-4-nitrophenyl | L2-A | 2.2/624.9 |
| 9 | 4-CF3-phenyl | L1-G | 3-CF3-4-nitrophenyl | L2-A | 1.96/610.9 |
| 10 | 4-CF3-phenyl | L1-H | 3-CF3-4-nitrophenyl | L2-A | 2.1/610.9 |
| 11 | 4-CF3-phenyl | L1-A | 3-CF3-4-CN-phenyl | L2-A | 2.2/590.9 |
| 12 | 4-CF3-phenyl | L1-A | 3-CF3—4SO₂NHEt-phenyl | L2-A | 2.08/673 |
| 13 | 4-CF3-phenyl | L1-C | 3-CF3-4-nitrophenyl | L2-A | 2.1/622.9 |
| 14 | 4-CF3-phenyl | L1-A | 3-F-4-CF₃-phenyl | L2-A | 2.41/583.2 |
| 15 | 4-CF3-phenyl | L1-A | 3-CF3-4-NH2-phenyl | L2-A | 1.46/580.2 |
| 16 | 4-CF3-phenyl | L1-A | 3-CF3-4-NHS(O2)—Et-phenyl | L2-A | 2.01/672.2 |
| 17 | 4-CF3-phenyl | L1-A | 3-CF3-4-nitrophenyl | L2-N | 2.4/624.2 |
| 18 | 4-CF3-phenyl | L1-B | 3-CF3-4-nitrophenyl | L2-A | 2.2/636.9 |
| 19 | 6-CF3-pyridin-3-yl | L1-A | 3-CF3-4-nitrophenyl | L2-A | 2.0/612.0 |
| 20 | 4-CF3-phenyl | L1-J | 3-CF3-4-nitrophenyl | L2-A | 1.8/584.8 |
| 21 | 4-CF3-phenyl | L1-A | 3-CF3-4-nitrophenyl | L2-R | 2.1/612.8 |
| 22 | 4-CF3-phenyl | L1-D | 3-CF3-4-nitrophenyl | L2-R | 2.1/626.8 |
| 23 | 4-CF3-phenyl | L1-A | 3-CF3-4-CN-phenyl | L2-B | 2.2/576.8 |
| 24 | 4-CF3-phenyl | L1-A | 3-S(O2)CH3-4-nitrophenyl | L2-A | 1.9/621.0 |
| 25 | 4-CF3-phenyl | L1-A | 3-CF3-4-nitrophenyl | L2-K | 2.2/582.8 |
| 26 | 4-CF3-phenyl | L1-D | 3-CF3-4-nitrophenyl | L2-K | 2.1/596.8 |
| 27 | 4-CF3-phenyl | L1-A | 4-OCF3-phenyl | L2-M | 2.2/631.8 |
| 28 | 4-CF3-phenyl | L1-A | 4-nitrophenyl | L2-M | 2/592.8 |
| 29 | 4-CF3-phenyl | L1-A | 4-methoxyphenyl | L2-D | 1.8/541.9 |
| 30 | 4-CF3-phenyl | L1-A | 4-tert-butylphenyl | L2-D | 2.2/567.9 |
| 31 | 4-CF3-phenyl | L1-A | 4-CF3-phenyl | L2-M | 2.2/615.8 |
| 32 | 4-CF3-phenyl | L1-A | 4-OCF3-phenyl | L2-D | 2/595.8 |
| 33 | 4-CF3-phenyl | L1-A | 4-CF3-phenyl | L2-D | 2/579.8 |
| 34 | 4-CF3-phenyl | L1-A | 4-CN-phenyl | L2-D | 1.8/536.8 |
| 35 | 4-CF3-phenyl | L1-A | 3-CF3-phenyl | L2-D | 2/579.9 |
| 36 | 4-CF3-phenyl | L1-A | 4-CF3-phenyl | L2-C | 1.8/565.8 |
| 37 | 4-CF3-phenyl | L1-A | 3-CF3-5-F-phenyl | L2-C | 1.3/583.8 |
| 38 | 4-CF3-phenyl | L1-A | 4-CN-phenyl | L2-C | 1.3/522.9 |
| 39 | 4-CF3-phenyl | L1-A | 3-CF3-4-F-phenyl | L2-C | 1.4/583.8 |
| 40 | 4-CF3-phenyl | L1-A | 4-F-phenyl | L2-D | 1.9/529.8 |
| 41 | 4-CF3-phenyl | L1-A | 3-CN-phenyl | L2-D | 1.8/536.8 |
| 42 | 4-CF3-phenyl | L1-A | 3-CN-phenyl | L2-C | 1.3/522.9 |
| 43 | 4-CF3-phenyl | L1-A | 2-CF3-phenyl | L2-D | 2/579.9 |
| 44 | 4-CF3-phenyl | L1-A | 3,5-bis(CF3)-phenyl | L2-D | 2.2/647.9 |
| 45 | 4-CF3-phenyl | L1-A | 4-OCF3-phenyl | L2-C | 1.4/581.9 |
| 46 | 4-CF3-phenyl | L1-A | 2,2-difluoro-1,3-benzodioxol-5-yl | L2-D | 2/591.8 |
| 47 | 4-CF3-phenyl | L1-A | 2,4,6-tri-F-phenyl | L2-C | 1.3/551.8 |
| 48 | 4-CF3-phenyl | L1-A | 4-SO2CF3-phenyl | L2-D | 2/643.8 |
| 49 | 4-CF3-phenyl | L1-A | 3,5-bis(CF3)-phenyl | L2-C | 1.4/633.9 |
| 50 | 4-CF3-phenyl | L1-A | 3-fluoro-4-OF3-phenyl | L2-C | 1.4/583.8 |
| 51 | 4-CF3-phenyl | L1-A | 3-OCF3-phenyl | L2-C | 1.4/581.9 |
| 52 | 4-CF3-phenyl | L1-A | 3,4,5-tri-F-phenyl | L2-C | 1.3/551.8 |
| 53 | 4-CF3-phenyl | L1-D | 3-CF3-4-CN-phenyl | L2-B | 1/590.9 |
| 54 | 4-CF3-phenyl | L1-E | 3-CF3-4-CN-phenyl | L2-B | 2/604.6 |
| 55 | 4-CF3-phenyl | L1-A | 3-CF3-4-nitrophenyl | L2-O₁ | 2.4/611.9 |
| 57 | 4-CF3-phenyl | L1-A | 3,4-bis(CF3)-phenyl | L2-B | 2.5/619.9 |
| 58 | 4-CF3-phenyl | L1-A | 3-nitro-4-CF3-phenyl | L2-B | 2.3/596.9 |
| 59 | 4-CF3-phenyl | L1-A | 3-CF3-4-CN-phenyl | L2-H | 1.5/590.9 |
| 60 | 4-CF3-phenyl | L1-A | 3-CF3-4-nitrophenyl | L2-H | 1.6/610.9 |
| 61 | 4-CF3-phenyl | L1-A | 3-CF3-4-CN-phenyl | L2-F | 1.5/575.9 |
| 62 | 4-CF3-phenyl | L1-D | 3-CF3-4-CN-phenyl | L2-F | 1.4/589.9 |
| 63 | 4-CF3-phenyl | L1-A | 3-CF3-4-CN-phenyl | L2-R | 2.1/592.9 |
| 64 | 4-CF3-phenyl | L1-D | 3-CF3-4-cyanophenyl | L2-R | 2/606.9 |
| 65 | 4-CF3-phenyl | L1-A | 3-CF3-4-CN-phenyl | L2-K | 2.2/562.8 |
| 66 | 4-CF3-phenyl | L1-D | 3-CF3-4-CN-phenyl | L2-K | 2.1/576.8 |
| 67 | 4-CF3-phenyl | L1-A | 3-CF3-4-nitrophenyl | L2-L | 2.3/611.9 |
| 68 | 4-CF3-phenyl | L1-D | 3-CF3-4-nitrophenyl | L2-L | 2.2/625.9 |
| 69 | 4-CF3-phenyl | L1-D | 3-CF3-4-nitrophenyl | L2-B | 2.7/611 |
| 70 | 4-CF3-phenyl | L1-D | 4-CF3-phenyl | L2-B | 2.9/566 |
| 71 | 4-CF3-phenyl | L1-D | 3-F-4-CF3-phenyl | L2-B | 2.9/584 |
| 72 | 4-CF3-phenyl | L1-D | 4-SCF3-phenyl | L2-B | 2.9/598 |
| 73 | 4-CF3-phenyl | L1-D | 3-CF3-4-aminophenyl | L2-B | 1.52/581 |
| 74 | 4-CF3-phenyl | L1-A | 3-CF3-4-cyanophenyl | L2-Q | 2.2/548.8 |
| 75 | 4-CF3-phenyl | L1-D | 3-CF3-4-CN-phenyl | L2-Q | 2.1/562.8 |
| 76 | 4-CF3-phenyl | L1-A | 3-CF3-4-CN-phenyl | L2-J | 2.1/576.9 |
| 77 | 4-CF3-phenyl | L1-D | 3-CF3-4-CN-phenyl | L2-J | 2/590.9 |
| 78 | 4-CF3-phenyl | L1-D | 3-CF3-4-nitrophenyl | L2-H | 1.5/624.9 |
| 79 | 4-CF3-phenyl | L1-D | 3-CF3-4-nitrophenyl | L2-F | 1.5/609.9 |
| 80 | 4-CF3-phenyl | L1-A | 3-nitro-4-CF3-phenyl | L2-B | 2.2/611 |
| 81 | 4-CF3-phenyl | L1-A | 3-CF3-4-nitrophenyl | L2-P | 2.2/582.9 |
| 82 | 4-CF3-phenyl | L1-I | 3-CF3-4-CN-phenyl | L2-B | 2/562.9 |
| 83 | 4-CF3-phenyl | L1-D | 3-CF3-4-nitrophenyl | L2-P | 2.1/597 |
| 84 | 4-CF3-phenyl | L1-A | 3-CF3-4-CN-phenyl | L2-G | 1.6/577 |
| 85 | 4-CF3-phenyl | L1-D | 3-CF3-4-CN-phenyl | L2-G | 1.6/591 |
| 86 | 4-CF3-phenyl | L1-D | 3,4-bis(CF3)-phenyl | L2-B | 2.41/634 |
| 87 | 4-CF3-phenyl | L1-A | 3-Cl-4-CN-phenyl | L2-B | 2.24/543 |
| 88 | 4-Cl-phenyl | L1-A | 3-CF3—4CN-phenyl | L2-B | 2.24/543 |
| 89 | 4-CF3-phenyl | L1-A | 3-CF3-4-nitrophenyl | L2-O₂ | 2.5/611.9 |
| 90 | 4-CF3-phenyl | L1-I | 3-CF3-4-nitrophenyl | L2-A | 2.54/596.9 |
| 91 | 4-Cl-phenyl | L1-D | 3-CF3-4-CN-phenyl | L2-B | 2.17/556.9 |
| 92 | 4-CF3-phenyl | L1-D | 3-Cl-4-CN-phenyl | L2-B | 2.19/556.8 |
| 93 | 4-CF3-phenyl | L1-A | 3-CF3-4-NHSO2benzyl-phenyl | L2-A | 2.36/735.1 |
| 94 | 4-Nitro-phenyl | L1-D | 3-CF3-4-CN-phenyl | L2-B | 1.90/567.9 |
| 95 | 3-CF₃-4-nitro-phenyl | L1-D | 3-CF3-4-CN-phenyl | L2-B | 2.04/635.9 |
| 96 | 4-CF3-phenyl | L1-L | 3-CF3-4-CN-phenyl | L2-B | 1.90/654.9 |
| 97 | 4-CH₃—S(O₂)—NH-phenyl | L1-D | 3-CF3-4-CN-phenyl | L2-B | 1.56/616.0 |
| 98 | 3-CF3-4-CH₃—S(O₂)—NH-phenyl | L1-D | 3-CF3-4-CN-phenyl | L2-B | 1.76/684.1 |
| 98a | 4-CF3-phenyl | L1-A | 2-CF3-4-CN-phenyl | L2-K₁ | 2.30/563.0 |

TABLE 2

| No. | $Z_1$ | $Z_2$ | $L_2$ | Retention Time (min.)/[MH]+ |
|---|---|---|---|---|
| 99  | N  | CH | L2-F | 1.45/595.3 |
| 100 | CH | N  | L2-F | 1.45/595.3 |
| 101 | N  | CH | L2-A | 1.4/610.4 |
| 102 | CH | N  | L2-A | 1.55/1.65/609.9 |

TABLE 3

| No. | $R_2$ | $R_2'$ | $L_1$ | $R_1$ | $R_1'$ | $L_2$ | $R_3$ | $R_3'$ | Retention Time (min.)/[MH]+ |
|---|---|---|---|---|---|---|---|---|---|
| 103 | $CF_3$ | H | L1-A | $N(CH_3)_2$ | H | L2-A | $NO_2$ | $CF_3$ | 2.2/654 |
| 104 | $CF_3$ | H | L1-A | H | $CH_3$ | L2-A | $NO_2$ | $CF_3$ | 2.5/624.9 |
| 105 | $CF_3$ | H | L1-A | $S(CH_3)$ | H | L2-A | $NO_2$ | $CF_3$ | 2.56/656.9 |
| 106 | $CF_3$ | H | L1-A | $CH_3$ | H | L2-A | $NO_2$ | $CF_3$ | 1.9/624.9 |
| 107 | $CF_3$ | H | L1-A | H | Cl | L2-A | $NO_2$ | $CF_3$ | 2.55/644.8 |
| 108 | Cl | H | L1-D | H | $CH_3$ | L2-B | CN | Cl | 2.3/536.9 |
| 109 | Cl | H | L1-A | H | $CH_3$ | L2-B | CN | Cl | 2.5/522.9 |
| 110 | $CF_3$ | H | L1-D | H | $CH_3$ | L2-A | $NO_2$ | $CF_3$ | 2.4/639 |
| 111 | $CF_3$ | H | L1-N | H | H | L2-A | $NO_2$ | $CF_3$ | 1.36/639.0 |
| 112 | $CF_3$ | H | L1-M | H | H | L2-A | $NO_2$ | $CF_3$ | 1.90/653.0 |
| 113 | $CF_3$ | H | L1-L | H | H | L2-A | $NO_2$ | $CF_3$ | 1.93/689.0 |
| 114 | CN | $CF_3$ | L1-A | H | H | L2-A | $NO_2$ | $CF_3$ | 2.05/636.1 |
| 115 | CN | $CF_3$ | L1-D | H | H | L2-A | $NO_2$ | $CF_3$ | 1.99/650.1 |
| 116 | $OCF_3$ | H | L1-D | H | H | L2-A | $NO_2$ | $CF_3$ | 1.91/641.0 |
| 117 | tert-Butyl | H | L1-A | H | H | L-2-B | CN | $CF_3$ | 2.51/564.7 |
| 118 | tert-Butyl | H | L1-D | H | H | L2-B | CN | $CF_3$ | 2.15/579.0 |
| 119 | $CF_3$ | H | L1-B | H | H | L2-B | CN | $CF_3$ | 2.24/562.9 |
| 120 | $CF_3$ | H | L1-A | H | H | L2-$K_1$ | CN | $CF_3$ | 2.24/562.9 |
| 121 | $CF_3$ | H | L1-A | H | H | L2-$K_2$ | CN | $CF_3$ | 2.23/562.9 |
| 122 | $CF_3$ | H | L1-A | H | H | L2-A | CN | $CF_3$ | 2.28/591.0 |
| 123 | $CF_3$ | H | L1-A | H | H | L2-B | $CF_3$ | CN | 2.30/576.9 |
| 124 | $CF_3$ | H | L1-D | H | H | L2-B | $CF_3$ | CN | 2.20/591.0 |
| 125 | $CF_3$ | H | L1-O | H | H | L2-B | CN | $CF_3$ | 2.14/591.0 |
| 126 | $CF_3$ | H | L1-D | H | H | L2-A | $SCF_3$ | H | 2.38/612.0 |
| 127 | $CF_3$ | H | L1-A | H | H | L2-A | $SCF_3$ | H | 2.54/598.0 |
| 128 | $CF_3$ | H | L1-D | H | H | L2-A | CN | $CF_3$ | 2.06/605.1 |
| 129 | $CF_3$ | H | L1-P | H | H | L2-A | $NO_2$ | $CF_3$ | 2.11/623.0 |
| 130 | $CF_3$ | H | L1-Q | H | H | L2-A | $NO_2$ | $CF_3$ | 2.15/639.1 |
| 131 | $CF_3$ | H | L1-A | H | H | L2-$O_2$ | $NO_2$ | $CF_3$ | 2.38/611.9 |

The anthelmintic potential of the novel compound is assessed in the following tests:

Gastro-Intestinal Larval Development Assay

Freshly harvested and cleaned nematode eggs are used to seed a suitably formatted well plate containing the test substances to be evaluated for antiparasitic activity and media allowing the full development of eggs through to 3rd instar larvae. The plates are incubated for 6 days at 25° C. and 60% relative humidity. Egg-hatching and ensuing larval development are recorded to identify a possible nematodicidal activity. Efficacy is expressed in percent reduced egg hatch, reduced development of L3, or paralysis & death of larvae at any stage. Compounds Nos. 2, 6-9, 11, 14, 15, 17, 19, 20, 23, 25, 53, 57, 58, 61, 62, 69, 71,79, 80, 82, 84, 85, 87, 88-90, 99-102, 106, 118, 121-124, and 131 reached ≥50% efficacy at 10 ppm, and are therefore considered active.

Gastro-Intestinal Worms in Gerbil

Gerbils are artificially infected by gavage with ca. 2000 third instar larvae each of *T. colubriformis* and *H. contortus* 7, respectively 6, days before treatment. Treatment is performed orally (p.o.) or subcutaneously (s.c.) with the formulated test compound. 3 days after treatment, gerbils are euthanised and dissected to recover *H. contortus* from stomach and *T. colubriformis* from upper part of midgut.

Efficacy is expressed as a percentage reduction in worm numbers in comparison with a placebo treated group, using the Abbot's formula. Compounds Nos. 2, 19, 96 and 101 showed an efficacy above 80% in gerbils at 32 mg/kg (p.o. or s.c.), and are therefore considered active.

Dirofilaria immitis Microfilaria Assay

Freshly harvested and cleaned Dirofilaria immitis microfilariae are prepared from blood from donor animals dogs. The microfialriae are then distributed in formatted microplates containing the test substances to be evaluated for antiparasitic activity. The plates are incubated for 48 hours at 25° C. and 60% relative humidity (RH). Motility of microfilariae is then recorded to determine efficacy. Efficacy is expressed in percent reduced motility as compared to the control and standards. Compounds Nos. 1-11, 13-26, 28-54, 57-90 99-104, 106-110, 118-125 and 127-131 showed an efficacy above 50% at 30 ppm, and are therefore considered active.

A. viteae in Gerbil.

Gerbils are artificially infected with 80 L3 larvae of A. viteae by subcutaneous injection. Treatment by gavage (p.o.) or by subcutaneous injection (s.c.) with the formulated test compounds occurs consecutively day 5 to day 9 after infection. Eighty-four days after infection, gerbils are bled for counting circulating microfilariae, using a Fuchs-Rosenthal counting chamber and microscope. Only test groups with an average of circulating microfilariae at least 50% lower than in the placebo treated group are fully dissected to recover adult worms. Efficacy is expressed as a % reduction in worm numbers in comparison with the placebo treated group, using the Abbot's formula. Compounds No. 2 (at 3 mg/kg p.o.), 6 (at 32 mg/kg p.o.), 18 (at 10 mg/kg p.o.), 57 (at 32 mg/kg p.o.), 65 (at 32 mg/kg p.o.), 80 (at 32 mg/kg p.o.), 90 (at 10 mg/kg p.o.), and 104 (at 23 mg/kg s.c.) showed an efficacy above 90% and are therefore considered active.

The invention claimed is:

1. A compound of formula

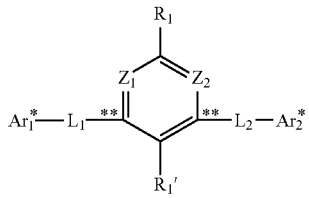

wherein one of $Z_1$ and $Z_2$ is N and the other one is CH; one of $R_1$ and $R_1'$ is H and the other one is H; $Ar_1$ is phenyl which is substituted by 1 or 2 same or different radicals selected from the group consisting of halogen and $C_1$-$C_2$-haloalkyl;

$Ar_2$ is phenyl which is substituted by 1 or 2 same or different radicals selected from the group consisting of halogen, cyano, nitro, $C_1$-$C_2$-haloalkyl, $C_1$-$C_2$-haloalkoxyl and $C_1$-$C_2$-haloalkylthio;

$L_1$ is a radical of formula

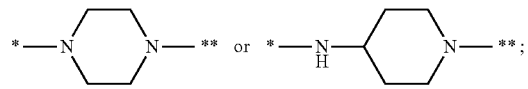

$L_2$ is a radical of formula

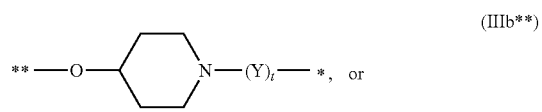

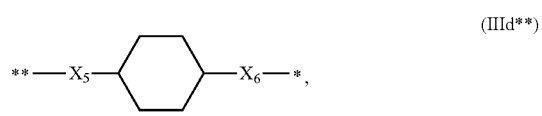

wherein Y is —$CH_2$— or —C(O)—, t is 0, $X_5$ is O, and $X_6$ is NH; or a physiologically acceptable salt thereof.

2. A composition for the control of parasites, which contains as active ingredient at least one compound of claim 1, in addition to carriers and/or dispersants.

3. A method of controlling endoparasites, on warm-blooded animals, which comprises administering to the warm-blooded animals a veterinary effective amount of at least one compound of claim 1.

* * * * *